US012686848B2

(12) United States Patent
Ahn

(10) Patent No.: US 12,686,848 B2
(45) Date of Patent: Jul. 21, 2026

(54) METHOD FOR PREPARING CELLULAR SPHEROID AND METHOD FOR PRODUCING EXTRACELLULAR VESICLES BY USING CELLULAR SPHEROID PREPARED BY SUCH METHOD

(71) Applicant: SPHEBIO CO., LTD., Pohang-si (KR)

(72) Inventor: Keunsun Ahn, Pohang-si (KR)

(73) Assignee: SPHEBIO CO., LTD., Pohang-si (KR)

( * ) Notice: Subject to any disclaimer, the term of this patent is extended or adjusted under 35 U.S.C. 154(b) by 646 days.

(21) Appl. No.: 18/043,002

(22) PCT Filed: Sep. 7, 2021

(86) PCT No.: PCT/KR2021/012079
§ 371 (c)(1),
(2) Date: Feb. 24, 2023

(87) PCT Pub. No.: WO2022/055210
PCT Pub. Date: Mar. 17, 2022

(65) Prior Publication Data
US 2023/0365921 A1      Nov. 16, 2023

(30) Foreign Application Priority Data

Sep. 11, 2020    (KR) ........................ 10-2020-0117144
Sep. 11, 2020    (KR) ........................ 10-2021-0052372

(51) Int. Cl.
*C12N 5/00*          (2006.01)
*C12N 13/00*         (2006.01)

(52) U.S. Cl.
CPC ........... *C12N 5/0062* (2013.01); *C12N 13/00* (2013.01); *C12N 2513/00* (2013.01); *C12N 2533/72* (2013.01); *C12N 2533/74* (2013.01); *C12N 2537/10* (2013.01)

(58) Field of Classification Search
None
See application file for complete search history.

(56) References Cited

FOREIGN PATENT DOCUMENTS

| | | | |
|---|---|---|---|
| EP | 3705294 | A1 | 9/2020 |
| KR | 10-2018-0032597 | A | 3/2018 |
| KR | 10-2019-0103166 | A | 9/2019 |
| KR | 10-2146682 | B1 | 8/2020 |
| KR | 10-2246224 | B1 | 4/2021 |
| WO | 2017-188487 | A1 | 11/2017 |

OTHER PUBLICATIONS

Koenen Biomolecules 2022, 12, 698, 15 pages (Year: 2022).*
Poldervaart et al., PLOS One, Aug. 2013, vol. 8, Issue 8, e72610, 9 pages (Year: 2013).*
Ashammakhi, N. et al., "Bioinks and bioprinting technologies to make heterogeneous and biomimetic tissue constructs", Elsevier, 2019, Materials Today Bio 1, document No. 100008, pp. 1-23.
International Search Report issued in PCT/KR2021/012079; mailed Dec. 14, 2021.

* cited by examiner

*Primary Examiner* — Evelyn Y Pyla
(74) *Attorney, Agent, or Firm* — Studebaker Brackett PLLC

(57) ABSTRACT

Proposed is a method of producing extracellular vesicles by using a cellular spheroid prepared by: preparing a first composition comprising cells and a heat-sensitive hydrogel dissolved in an ionic solution; dispensing the first composition drop by drop into a second hydrogel; forming core-shell structures by causing a reaction between the second hydrogel and the ionic solution along an outer surface of a droplet of the first composition injected into the second hydrogel to form a cross-linked hydrogel shell; changing a temperature so that the heat-sensitive hydrogel in the cross-linked hydrogel shell undergoes a phase change from a gel phase to a liquid phase; and forming a cellar spheroid by allowing the inside of the cross-linked hydrogel shell to be changed into the liquid phase and allowing the cells to precipitate and aggregate. Furthermore, the extracellular vesicles can be produced by using the cellular spheroids prepared thereby.

8 Claims, 7 Drawing Sheets

(a)                    (b)                    (c)

Solution A

Solution B

[S1]        [S2]        [S3]

(...T)        Spheroid formation (a)          (b)

(a)          (b)

METHOD FOR PREPARING CELLULAR SPHEROID AND METHOD FOR PRODUCING EXTRACELLULAR VESICLES BY USING CELLULAR SPHEROID PREPARED BY SUCH METHOD

CROSS-REFERENCE TO RELATED APPLICATIONS

This application is a U.S. National Phase Entry of International Application No. PCT/KR2021/012079 filed on Sep. 7, 2021, which claims the benefit of priority to Korean Patent Application No. 10-2020-0117144 and 10-2021-0052372 filed on Sep. 11, 2020, the entire content of which is incorporated herein by reference.

TECHNICAL FIELD

The present invention relates to a method of preparing a cellular spheroid inside core-shell structures, the structures formed in situ by dispensing droplets containing cells, an ionic solution, and a heat-sensitive hydrogel into an ionic cross-linked hydrogel, and to a method of producing an extracellular vesicle using the cellular spheroid prepared thereby.

BACKGROUND ART

Most cellular structures constituting human and animal bodies are organized in three-dimensional structures. Such three-dimensional structures of cells lead to complex cell-to-cell interactions that are difficult for cell culture products having a two-dimensional monolayer structure to imitate.

Although cells behave more naturally when cultured in a three-dimensional environment, there are problems in that three-dimensional cell culture products are difficult to be formed, and costs are high. Existing in vitro cell culture can only provide typical two-dimensional cell culture models.

A cellular spheroid is one example of the typical three-dimensional cell culture models and has been applied to basic research and clinical pharmacology. Such a cellular spheroid means an aggregated cell cluster with a diameter of about several hundreds of micrometers.

As existing methods of forming cellular spheroids, there are dynamic culture methods, such as a hanging drop method or rotary agitation. However, culture of the cellular spheroids formed by such methods may take up to about four days, and the success rate thereof is also remains at about 50%. In addition, there is a problem in that cell culture medium is difficult to be exchanged, and cell loss thus occurs in the process of exchange.

In several existing methods of preparing cellular spheroids, a scaffold dish capable of preparing the cellular spheroids can be used, or cells can be aggregated in vitro. In addition, the hanging drop method can be used to prepare the cellular spheroids. Furthermore, as another existing method for preparing cellular spheroids, there is a method of preparing cellular spheroids by injecting cells into microwells to which cells are unable to be attached and then inducing aggregation of the injected cells.

However, in the case of such a method, complex and lengthy microfabrication processes involving photolithography and soft lithography are required to fabricate the microwells.

Even with such a method of preparing cellular spheroids using microwells, there are still problems in that size control of the cellular spheroids is difficult, and the process of recovering or harvesting the prepared cellular spheroids is difficult to be performed.

DISCLOSURE

Technical Problem

To effectively solve the problems of the related art as described above, the present invention provides a method of continuously preparing a cellular spheroid by dispensing a first composition containing cells and a heat-sensitive hydrogel dissolved in an ionic solution into a second hydrogel, causing a reaction between the second hydrogel and the ionic solution along an outer surface of the first composition injected into the second hydrogel to form a cross-linked hydrogel shell, and allowing the cells to precipitate and aggregate in the cross-linked hydrogel shell. In addition, the present invention provides a cellular spheroid prepared thereby.

Furthermore, the present invention is to provide a method of producing extracellular vesicles (exosomes) by using the continuously prepared and recovered cellular spheroids as described above, and to provide extracellular vesicles (exosomes) mass-produced thereby.

Technical Solution

A method of preparing a cellular spheroid, according to one embodiment of the present invention, includes: preparing a first composition containing cells and a heat-sensitive hydrogel dissolved in an ionic solution; dispensing the first composition drop by drop into a second hydrogel; forming core-shell structures by causing a reaction between the second hydrogel and the ionic solution along an outer surface of a droplet of the first composition injected into the second hydrogel to form a cross-linked hydrogel shell; changing a temperature so that the heat-sensitive hydrogel in the cross-linked hydrogel shell undergoes a phase change from a gel phase to a liquid phase; and forming a cellular spheroid by allowing the inside of the cross-linked hydrogel shell to be changed into the liquid phase and allowing the cells to precipitate and aggregate to form the cellular spheroid.

The heat-sensitive hydrogel may contain any one or more selected from the group consisting of gelatin, Pluronic F127, or poly(N-isopropylacrylamide). In addition, the second hydrogel preferably contains any one or more selected from the group consisting of alginate and chitosan. Furthermore, the ionic solution may contain any one or more kinds of ions selected from the group consisting of calcium ions and potassium ions.

In the dispensing, a size of the droplet of the first composition being dispensed may be controlled by varying discharge conditions such as a discharge volume or discharge time.

After the forming of the cellular spheroid, collecting the cellular spheroid from hollow structures produced by degradation of the cross-linked hydrogel shell may be further included. The collecting of the cellular spheroid may be performed by a method using any one or more selected from among enzymes, heat, electric fields, and magnetic fields.

As another embodiment of the present invention, a cellular spheroid prepared thereby may be included.

As a further embodiment of the present invention, a method of producing extracellular vesicles using a cellular spheroid may be included. The method includes: preparing a first composition containing cells and a heat-sensitive hydrogel dissolved in an ionic solution; dispensing the first composition drop by drop into a second hydrogel; forming core-shell structures by causing a reaction between the second hydrogel and the ionic solution along an outer surface of a droplet of the first composition injected into the second hydrogel to form a cross-linked hydrogel shell; changing a temperature so that the heat-sensitive hydrogel in the cross-linked hydrogel shell undergoes a phase change from a gel phase to a liquid phase; forming cellular spheroid by allowing the inside of the cross-linked hydrogel shell to be changed into the liquid phase and allowing the cells to precipitate and aggregate to form the cellular spheroid; and culturing the cellular spheroid to obtain extracellular vesicles.

The heat-sensitive hydrogel may contain any one or more selected from the group consisting of gelatin, Pluronic F127, or poly(N-isopropylacrylamide). In addition, the second hydrogel preferably contains any one or more selected from the group consisting of alginate and chitosan. Furthermore, the ionic solution may contain any one or more kinds of ions selected from the group consisting of calcium ions and potassium ions.

In the dispensing, a size of the droplet of the first composition being dispensed may be controlled by varying discharge conditions such as a discharge volume or discharge time.

Collecting the cellular spheroid from hollow structures produced by degradation of the cross-linked hydrogel shell may be further included between the forming of the cellular spheroid and the obtaining of the extracellular vesicles. The collecting of the cellular spheroid may be performed by a method using any one or more selected from among enzymes, heat, electric fields, and magnetic fields.

Extracellular vesicles prepared thereby may also be included as a further embodiment of the present invention.

Advantageous Effects

In existing methods of preparing cellular spheroids, there are problems in that between-worker variability is high, a large amount of work is required, and a process takes a long time. In addition, quality control is difficult, so mass production is difficult. Compared to the existing methods, the method of preparing the cellular spheroid and/or the method of producing the extracellular vesicles, according to the present invention, has excellent repeatability. As a result, there are advantages in that quality control and rapid mass production are facilitated.

In addition, as cells aggregate in an empty space inside a cross-linked hydrogel shell, a discharge amount of a composition is controlled. Therefore, a size of the obtained cellular spheroid can be controlled, and cell contamination can be effectively prevented. In addition, the cellular spheroids that are intact and stable can be effectively obtained.

Through the method of preparing the cellular spheroid according to the present invention, uniform and stable cellular spheroids can be mass-produced with a high yield. In addition, there is an advantage in that exosomes can be effectively produced or obtained in large quantities by culturing such prepared cellular spheroids.

In addition, the cellular spheroid, prepared according to one embodiment of the present invention, can be effectively applied to various bio-industries for development of drug test chips for new drug development and artificial tissue mimetics for tissue regeneration, and is thus industrially applicable.

Figure 1:
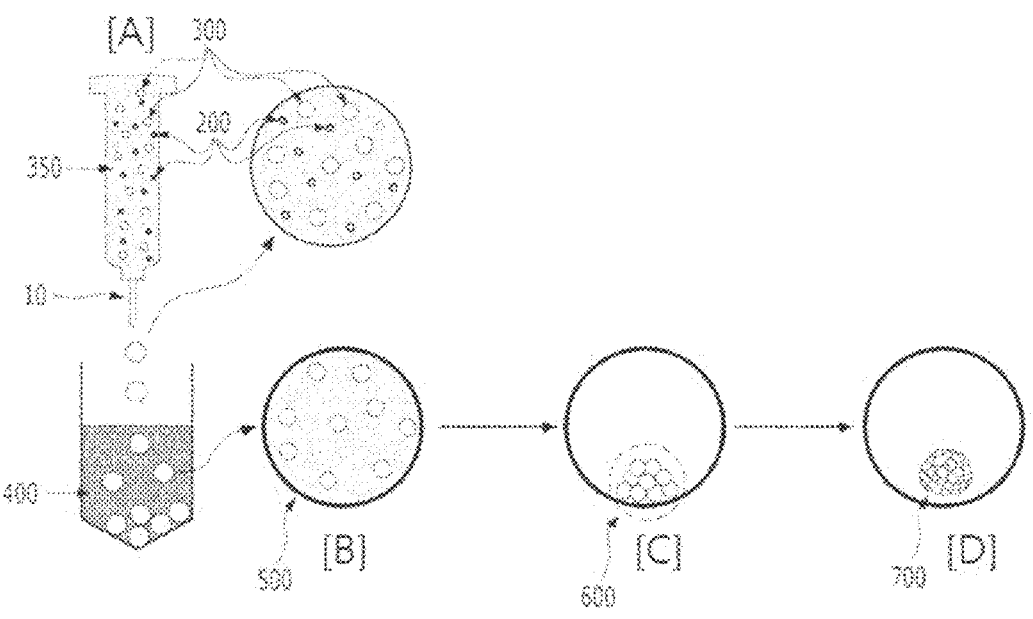
FIG. 1 is a diagram schematically illustrating a process of preparing a cellular spheroid according to an embodiment of the present invention.

| [EXPLANATION OF REFERENCE NUMERALS] | | | |
|---|---|---|---|
| 10: | NOZZLE | 100: | HEAT-SENSITIVE HYDROGEL |
| 200: | ION | 300: | CELL |
| 350: | FIRST COMPOSITION | 400: | SECOND HYDROGEL |
| 500: | HYDROGEL SHELL | 600: | PRECIPITATED CELLS |
| 700: | CELLULAR SPHEROID | | |

BEST MODE

Prior to the detailed description with reference to the preferred embodiments of the present invention, the terms or words used in the claims of this specification should not be interpreted as being limited to common or dictionary meanings, but should be interpreted as having meanings and concepts that are defined within the technical scope of the present invention.

Unless the context clearly indicates otherwise, it will be further understood that the terms "comprises", "comprising", "includes", and/or "including", when used herein, specify the presence of other elements, but do not preclude the presence or addition of other elements.

Hereinafter, an embodiment of the present invention will be described. However, the scope of the present invention is not limited to the following preferred embodiments, and those skilled in the art can implement various modified forms of the contents described in this specification within the scope of the present invention.

A method of preparing a cellular spheroid, according to an embodiment of the present invention, includes: preparing a first composition containing cells and a heat-sensitive hydrogel dissolved in an ionic solution; dispensing the first composition into a second hydrogel; forming a cross-linked hydrogel shell by causing a reaction between the second hydrogel and the ionic solution along an outer surface of the first composition injected into the second hydrogel; and forming a cellular spheroid by allowing the cells to precipitate and aggregate in the cross-linked hydrogel shell (see FIG. 1).

The ionic solution is not particularly limited provided that the ionic solution can easily dissolve the heat-sensitive hydrogel and cross-link the second hydrogel. The ionic solution preferably contains any one or more kinds of ions selected from the group consisting of calcium ions and potassium ions, and a calcium chloride aqueous solution may be used.

The first composition is a homogeneous mixture of living cells in the ionic solution in which the heat-sensitive hydrogel is dissolved. In the first composition, about $10^3$ to $10^8$ of the living cells may be contained, and a concentration of the ions in the ionic solution may be in a range of about 10 mM to 700 mM. When the ion concentration is excessively low, the hydrogel shell to be formed in a post-process may not be formed. When the ion concentration is excessively high, there may be a problem in that a thickness of the shell is excessively large, so a space in which the cellular spheroid is to be formed may be insufficient, or the shell is formed with an uneven thickness.

The heat-sensitive hydrogel may be dissolved in a range of about 1 part to 10 parts by weight with respect to 100 parts by weight of the ionic solution. When the heat-sensitive hydrogel does not for within the above composition range, the dispensing, which is a post-step, may be difficult to be performed, or a dispensed shape may be uneven.

In the dispensing, the first composition satisfying the above composition component and composition range is dispensed into a storage tank in which the second hydrogel is stored by using a pipette, a dispenser, or a 3D printer. Preferably, in the dispensing, the first composition is evenly dispensed in a predetermined amount. This is because the uniformity of the cellular spheroid to be formed in the post-step and the rate of producing an extracellular vesicles produced by using such cellular spheroid may be affected.

When the first composition, dispensed into the storage tank in which the second hydrogel is stored, comes into contact with the second hydrogel, the second hydrogel and the ionic solution contained in the first composition are cross-linked by an in-situ reaction. As a result, the hydrogel shell is formed on the outer perimeter of the first composition being dispensed.

The hydrogel shell, formed along the outer surface of the first composition being dispensed, is formed when the second hydrogel undergoes an instantaneous cross-linking reaction caused by the ionic solution. Thus, hollow structures, in which the living cells and the ionic solution that is unable to be involved in the formation of the heat-sensitive hydrogel and the hydrogel shell exist, are formed.

Any one or more selected from the group consisting of gelatin, Pluronic F127, or poly(N-isopropylacrylamide) may be used as the heat-sensitive hydrogel. In addition, any one or more selected from alginate and chitosan may be used as the second hydrogel.

Such a heat-sensitive hydrogel may undergo a phase change due to a temperature change in the forming of the cellular spheroid below. For example, a temperature of the storage tank in which the second hydrogel is stored may be raised to about 30° C. or higher to change a gel phase of the heat-sensitive hydrogel existing in the hydrogel shell, formed in situ in a hollow-sphere shape, to a liquid phase.

Preferably, the heat-sensitive hydrogel contains any one or more selected from the group consisting of gelatin, Pluronic F127, or poly(N-isopropylacrylamide). In addition, the second hydrogel may contain any one or more selected from the group consisting of alginate and chitosan. Preferably, the ionic solution further contains any one or more kinds of ions selected from the group consisting of calcium ions and potassium ions.

The phase of the heat-sensitive hydrogel existing inside the hollow hydrogel shell is changed as described above, so the cells coexisting with the heat-sensitive hydrogel inside the hollow hydrogel shell naturally sink downward in the hollow hydrogel shell due to the gravity force.

While such precipitated cells undergo the cellular spheroid formation, the temperature is changed so that the phase of the heat-sensitive hydrogel in the cross-linked hydrogel shell is changed. As a result, with cell precipitation occurring inside the hollow hydrogel shell, the cells naturally form the cellular spheroid.

Therefore, in the dispensing, a size of the first composition to being dispensed is preferably controlled by varying discharge conditions. This is because a size of the hollow hydrogel shell, in which the cellular spheroid is formed, is determined by discharge time or discharge volume.

When the cellular spheroid is formed in the hollow hydrogel shell as described above, collecting the cellular spheroid by degradation of the cross-linked hydrogel shell may be further performed. The degradation process of such a cross-linked hydrogel shell may be performed by various methods that are conventionally known. For example, the degradation process may be performed by appropriate methods that hardly affect the cellular spheroid, such as degradation with enzymes, heat, electric fields, magnetic fields, and the like.

As another embodiment of the present invention, a three-dimensional cellular spheroid prepared through such processes may be provided. The three-dimensional cellular spheroid cultured in 3D culture, according to the present invention, has the most similar characteristics to an actual cellular spheroid, compared to a cellular spheroid obtained through existing two-dimensional culture. In addition, there is an advantage in that a large number of the extracellular vesicles can be rather easily obtained without applying additional external stimuli or conditions.

Thus, a yet another embodiment of the present invention includes a method of obtaining extracellular vesicles from the cellular spheroid obtained by such a method of preparing the cellular spheroid, and extracellular vesicles obtained thereby.

Hereinafter, specific functions and effects of the present invention will be described with reference to specific embodiments of the present invention. However, the embodiments of the present invention are disclosed for illustrative purposes and are not intended to limit the scope of the present invention.

Preparation Example 1: Preparation of First Mixture $6\times10^5$ cells (for example, MIN-6 cells) were prepared by cell culture and suspended in 1 ml of culture media to evenly distribute the cells therein.

Gelatin powder (cold water fish or porcine skin) was dissolved in distilled water to prepare 1 ml of a gelatin solution in an amount of 10% by weight. Then, $CaCl_2$ (calcium chloride, molecular weight: 111.0, purchased from Sigma Aldrich) was added to the gelatin solution so that a concentration thereof was 500 mM, thereby preparing a bio-ink (first mixture) containing 5% by weight of gelatin and the cells.

Preparation Example 2

A container with an open top was filled with a prepared 5% alginate solution. Then, the container was placed under a volumetric precision dispenser, and the bio-ink (first mixture) prepared in Preparation Example 1 was transferred to a syringe for the volumetric precision dispenser. Next, the remaining bubbles inside the syringe and the volumetric precision dispenser were removed.

The bio-ink was dispensed from the dispenser with a 200-μm inner diameter nozzle under predetermined conditions of discharge volumes (in a range of 100 nl to 700 nl) and discharge time (1 second per shot). In this case, the position of the dispenser was adjusted so that the discharge products of the bio-ink (first mixture) dispensed with the driving control of x-y-z stages connected with the dispenser were able to maintain uniform intervals without overlapping each other.

Calcium ions contained in the dispensed bio-ink were ionically crosslinked in situ as the alginate solution with which the container was filled came into contact, and the bio-ink, the first mixture, formed hollow sphere-shaped beads.

In this case, sizes of the hollow sphere-shaped beads being produced were examined by varying the discharge volumes of the bio-ink. The results thereof are shown in Table 1 below.

TABLE 1

Figure 2:
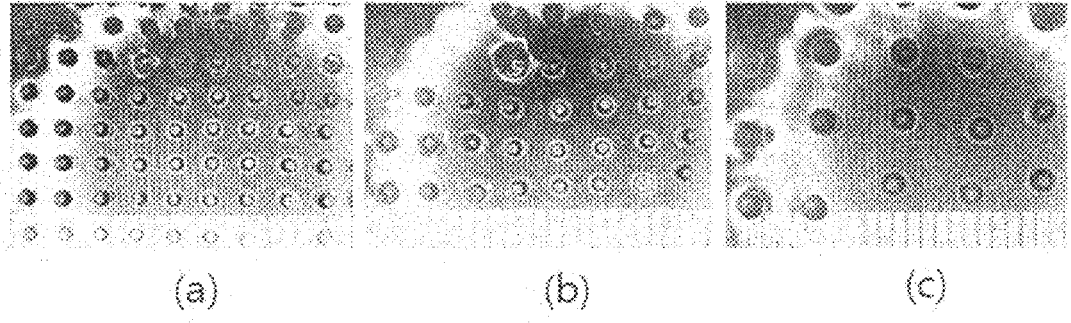
FIG. 2 is a diagram of observation results of a size change of hollow sphere-shaped beads in which a cross-linked hydrogel shell is formed depending on discharge volumes in a preparation process according to an embodiment of the present invention.

| Discharge volume of bio-ink [nl] | 100 | 200 | 700 |
|---|---|---|---|
| Discharge time [sec] | | 1 | |
| Nozzle size [μm] | | 200 | |
| Hollow sphere-shaped bead diameter [mm] | 1 | 1.4 | 2 |
| FIG. 2 | (a) | (b) | (c) |

As confirmed by the results of Table 1 above, it is seen that the diameter of the hollow sphere-shaped bead produced in situ is able to be effectively controlled by controlling the discharge volume of the bio-ink (first mixture). Such a dispensing process was performed at room temperature. The Peltier cooling system with a temperature control function along an outer surface of the dispenser syringe can be added, as needed.

Preparation Example 3

200 nl of the bio-ink was dispensed in the same manner as in Preparation Examples 1 and 2, and fluorescence staining was performed to observe a cell aggregation process in hollow sphere-shaped beads.

A cell-tracking dye is a non-fluorescent dye, but is a hydrophobic material that emits fluorescence when entering living cells. The cell-tracking dye can easily penetrate the living cells and has an advantage in that fluorescent materials remain even after cell division and can be thus confirmed in proliferating cells.

In this Preparation Example, MIN-6 cells were fluorescently stained using a cell-tracking dye kit. $5\times10^6$ living cells were prepared, washed with 1×PBS, and then added to a tracking dye green working solution to cause reactions at a temperature of about 37° C. for about 30 minutes.

The cells were made into pellets by centrifugation after being washed with HHBS three times, and 1 ml of DMEM was added thereto to prepare a cell suspension. Thereafter, the cell suspension was mixed with a hydrogel and underwent the same process of Preparation Examples 1 and 2 mentioned above. Then, the fluorescently stained cells were confirmed at a wavelength of 490/525 nm.

Figure 3:
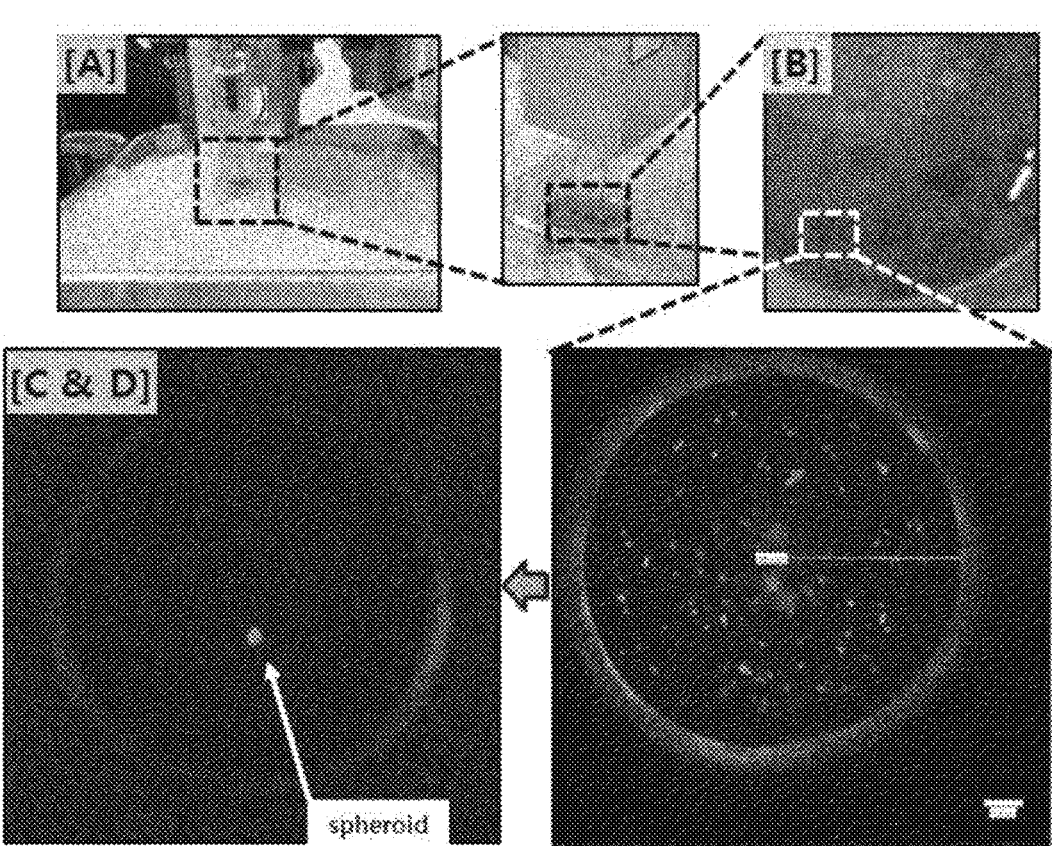
FIG. 3 is a diagram sequentially showing observation results of a process of obtaining an actual cellular spheroid by a preparation method according to an embodiment of the present invention.

As confirmed in the results of FIG. 3, the hollow sphere-shaped beads were formed in the alginate solution by dispensing the bio-ink using the volumetric precision dispenser. In addition, the cellular spheroid of the living cells inside the hollow sphere-shaped bead were confirmed.

Preparation Example 4

Figure 4:
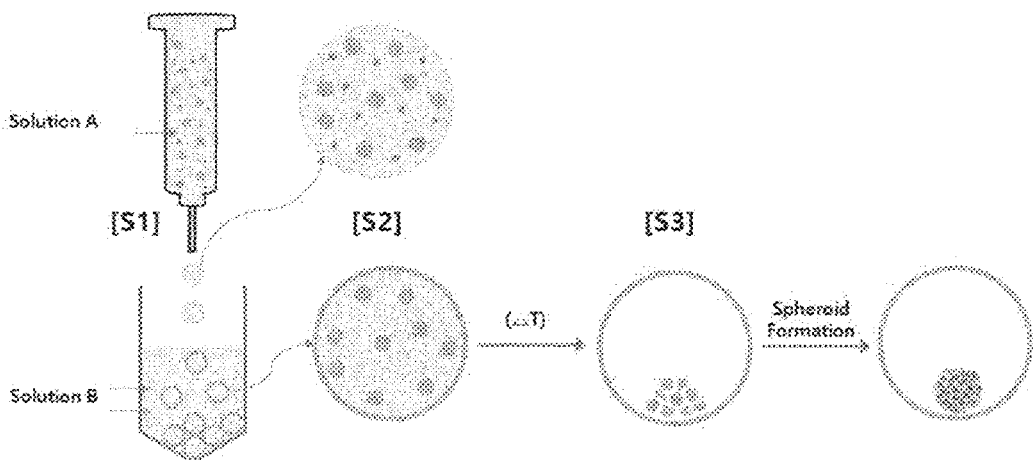
FIG. 4 is a diagram schematically illustrating a process of producing an extracellular vesicle according to another embodiment of the present invention.

As another embodiment of the present invention, a method of producing extracellular vesicles using a cellular spheroid is to be described. As shown schematically in FIG. 4, gelatin powder in which 5% of gelatin (bovine skin, type B, Sigma Aldrich) was provided in powder form was dissolved in a tertiary distilled water at a temperature of 70° C. Then, calcium chloride ($CaCl_2$) having a concentration in a range of 10 mM to 30 mM was added to prepare Solution A.

Solution B was prepared by dissolving alginate powder provided in sodium alginate (Sigma Aldrich) powder form in a tertiary distilled water with a concentration in a range of 0.5% to 2% at room temperature.

In this case, human mesenchymal stromal cells (hMSCs) cultured using α-MEM (FBS 10%, Antibiotic-Antimycotic 1%) were mixed with Solution A having a concentration in range of $1\times10^5$ cell/ml to $10\times10^5$ cells/ml at room temperature 2 ml of such prepared Solution A and the hMSCs ($3\times10^5$ cells/ml) were mixed at room temperature using a pipette and supplied to a syringe of a precision injection module as materials.

Solution A was dispensed into prepared Solution B in a conical tube prepared in advance after setting conditions: a pneumatic pressure of the precision injection module of 50 kPa, a discharge amount of droplets of about 4 μL, and a discharge time of 0.05 seconds (S1).

Solution A droplets in which the cells were mixed come into contact with Solution B and form beads in which a shell was formed by ionic cross-linking (S2).

The beads were removed from Solution B and transferred to a cell culture container. A cell culture medium was added thereto, and the beads were incubated in an incubator environment (a temperature of 37° C.) for 12 hours, so that the cells aggregated therein (S3).

Figure 5:
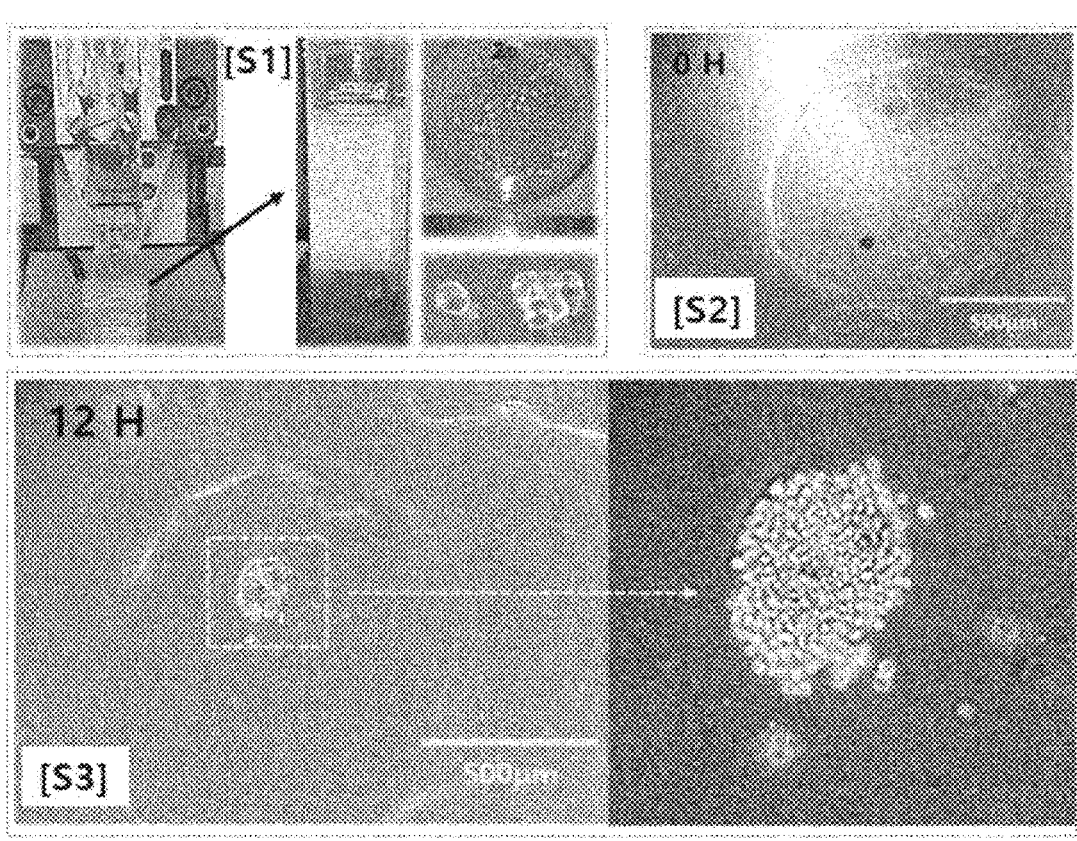
FIG. 5 is a diagram showing each step (S1, S2, and S3) actually tested according to the method proposed in FIG. 4.

The actual observation results for the processes of S1 to S3 were presented in a diagram of FIG. 5.

Preparation Example 5

Figure 6:
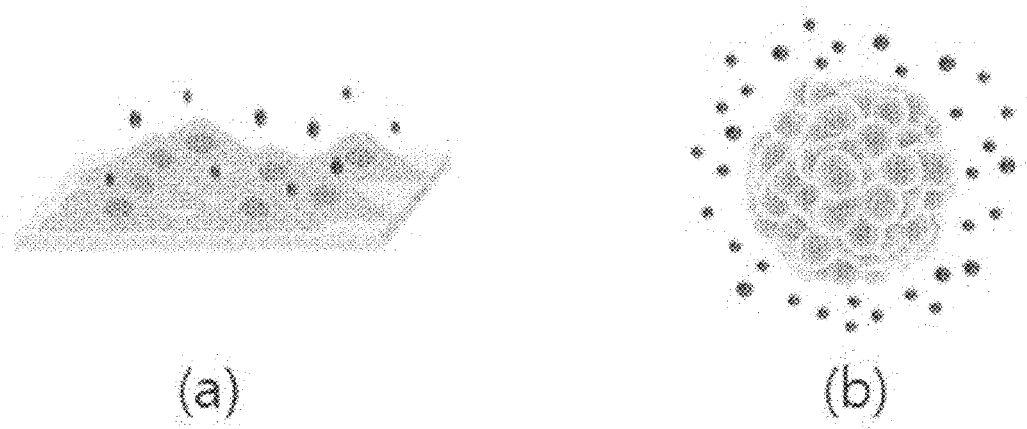
FIGS. 6A and 6B are diagram schematically illustrating conventional 2D cell culture and 3D cellular spheroid culture, respectively, according to the present invention.
Figure 7:
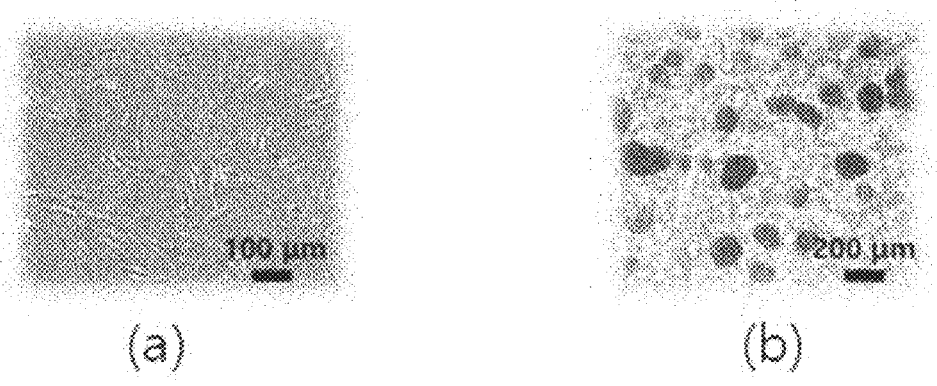
FIGS. 7A and 7B are diagrams showing observation results of conventional 2D cell culture and 3D cellular spheroid culture, respectively, according to the present invention.

To confirm the production efficiency of extracellular vesicles produced by 3D culture using a cellular spheroid according to the embodiment of the present invention, extracellular vesicles were produced by conventional two-dimensional cell culture and compared.

α-MEM (Exosome-depleted FBS 10%, Antibiotic-Antimycotic 1%) was used to culture hMSCs ($3\times10^5$ cells/ml) in a cell culture vessel. After two days of culture, EVs were extracted using a separation kit product and was quantitatively analyzed (see FIGS. 6A and 7A).

α-MEM (Exosome-depleted FBS 10%, Antibiotic-Antimycotic 1%) was used to culture the cellular spheroid obtained in Preparation Example 4. After two days of culture, EVs were extracted using a separation kit product, and each of the EVs was quantitatively analyzed (see FIGS. 6B and 7B).

Figure 8:
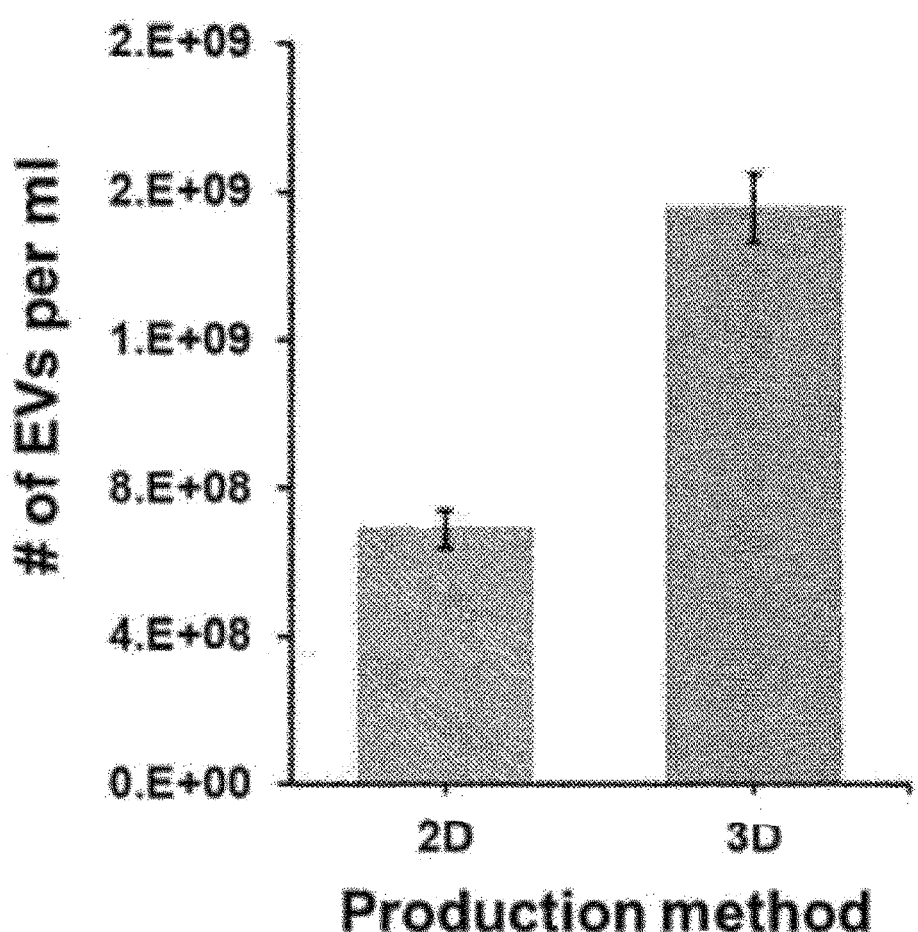
FIG. 8 is a diagram showing summary results for conventional 2D cell culture and 3D cellular spheroid culture according to the present invention, the summary quantitatively comparing yields of extracellular vesicles (EVs) obtained per volume of culture medium.
Figure 9:
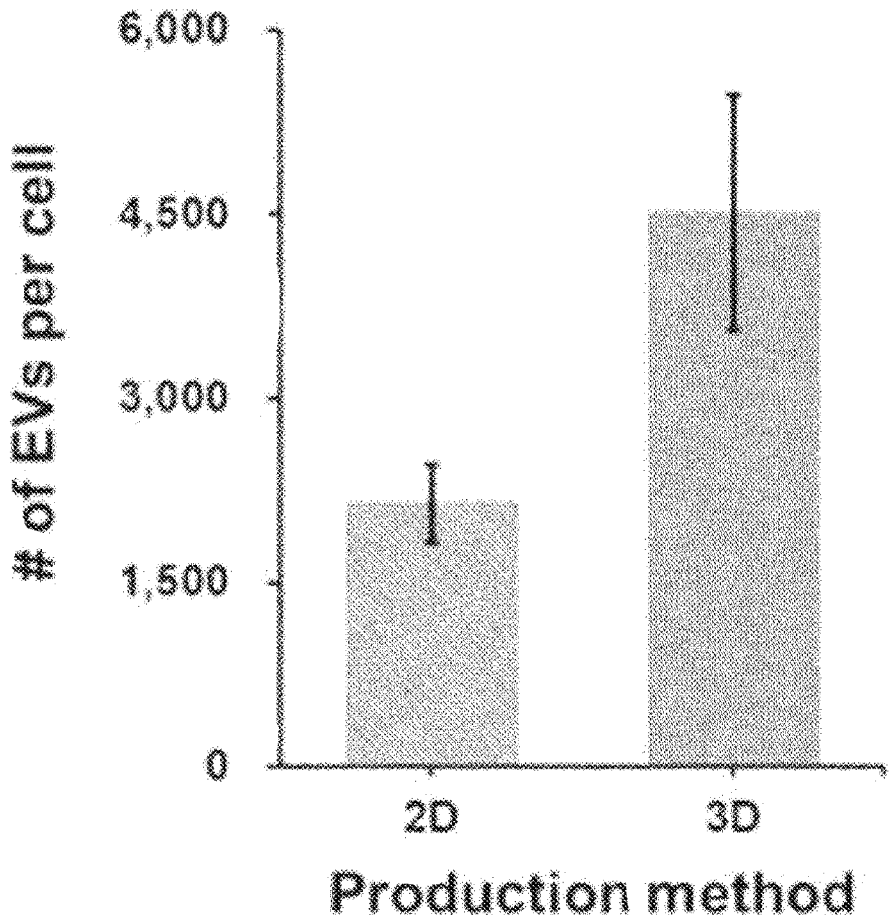
FIG. 9 is a diagram showing results of quantitatively comparing yields of extracellular vesicles (EVs) obtained per cell.

As confirmed by the results of FIGS. 8 and 9, as a result of comparing EV production amount per culture medium volume (ml) (FIG. 8) with EV production amount per cell (FIG. 9), it was confirmed that the EV production amount was higher in the 3D culture using the cellular spheroid according to the present invention than in the existing two-dimensional cell culture. Thus, the three-dimensional cell culture technology using the cellular spheroid prepared according to the present invention is seen to be a method of effectively producing the extracellular vesicles (EVs).

The present invention is not limited to specific embodiments and descriptions stated above. Those skilled in the art will appreciate that various modifications are possible, without departing from the scope and spirit of the invention as disclosed in the accompanying claims, and such modifications will fall within the protection scope of the present invention.

INDUSTRIAL APPLICABILITY

The present invention provides a method of continuously preparing a cellular spheroid by dispensing a first composition containing cells and a heat-sensitive hydrogel dissolved in an ionic solution into a second hydrogel, causing a reaction between the second hydrogel and the ionic solution along an outer surface of the first composition injected into the second hydrogel to form a cross-linked hydrogel shell, and then allowing the cells to precipitate and aggregate in the cross-linked hydrogel shell. In addition, the present invention provides a cellular spheroid prepared thereby. Furthermore, extracellular vesicles, such as exosomes, can be prepared by culturing such prepared cellular spheroids.

In existing methods of preparing cellular spheroids, there are problems in that between-worker variability is high, a large amount of work is required, and a process takes a long time. In addition, quality control is difficult, so mass production is difficult. Compared to the existing methods, the method of preparing the cellular spheroid and/or the method of producing the extracellular vesicles, according to the present invention, has excellent repeatability. As a result, there are advantages in that quality control and rapid mass production are facilitated. Such cellular spheroids and/or extracellular vesicles prepared thereby can be effectively applied to various bio-industries for development of drug test chips for new drug development and artificial tissue mimetics for tissue regeneration, and is thus industrially applicable.

The invention claimed is:

1. A method of preparing a cellular spheroid, the method comprising:

preparing a first composition comprising cells and a heat-sensitive hydrogel dissolved in an ionic solution;

dispensing the first composition drop by drop into a second hydrogel;

forming a core-shell structure by causing a reaction between the second hydrogel and the ionic solution in the first composition along an outer surface of a droplet of the first composition injected into the second hydrogel to form a cross-linked hydrogel shell only on the outer surface of the droplet of the first composition;

changing a temperature so that the heat-sensitive hydrogel in the cross-linked hydrogel shell undergoes a phase change from a gel phase to a liquid phase;

forming a cellular spheroid by allowing the inside of the cross-linked hydrogel shell to be changed into the liquid phase and allowing the cells to precipitate and aggregate to form the cellular spheroid, and recovering the cellular spheroid from a hollow structure produced by degradation of the cross-linked hydrogel shell without an enzyme, wherein a concentration of ions in the ionic solution is in a range of 10 mM to 700 mM, wherein the recovering of the cellular spheroid is performed by a method using any one or more selected from among heat, an electric field, and a magnetic field, and wherein the heat-sensitive hydrogel comprises one or more selected from the group consisting of Pluronic F127 and poly(N-isopropylacrylamide).

2. The method of claim 1, wherein the second hydrogel comprises any one or more selected from the group consisting of alginate and chitosan.

3. The method of claim 1, wherein the ionic solution comprises any one or more kinds of ions selected from the group consisting of calcium ions and potassium ions.

4. The method of claim 1, wherein in the dispensing, a size of the droplet of the first composition being dispensed is controlled by varying a discharge volume or discharge time.

5. A method of producing an extracellular vesicle using a cellular spheroid, the method comprising:

preparing a first composition comprising cells and a heat-sensitive hydrogel dissolved in an ionic solution;

dispensing the first composition drop by drop into a second hydrogel;

forming a core-shell structure by causing a reaction between the second hydrogel and the ionic solution in the first composition along an outer surface of a droplet of the first composition injected into the second hydrogel to form a cross-linked hydrogel shell only on the outer surface of the droplet of the first composition;

changing a temperature so that the heat-sensitive hydrogel in the cross-linked hydrogel shell undergoes a phase change from a gel phase to a liquid phase;

forming a cellular spheroid by allowing the inside of the cross-linked hydrogel shell to be changed into the liquid phase and allowing the cells to precipitate and aggregate to form the cellular spheroid;

recovering the cellular spheroid from a hollow structure produced by degradation of the cross-linked hydrogel shell without an enzyme; and culturing the cellular spheroid to obtain an extracellular vesicle, wherein a concentration of ions in the ionic solution is in a range of 10 mM to 700 mM, wherein the recovering of the cellular spheroid is performed by a method using any one or more selected from among heat, an electric field, and a magnetic field, and wherein the heat-sensitive hydrogel comprises one or more selected from the group consisting of Pluronic F127 and poly(N-isopropylacrylamide).

6. The method of claim 5, wherein the second hydrogel comprises any one or more selected from the group consisting of alginate and chitosan.

7. The method of claim 5, wherein the ionic solution comprises any one or more kinds of ions selected from the group consisting of calcium ions and potassium ions.

8. The method of claim 5, wherein in the dispensing, a size of the droplet of the first composition being dispensed is controlled by varying a discharge volume or discharge time.

* * * * *